(12) United States Patent
Malherbe et al.

(10) Patent No.: US 8,076,495 B2
(45) Date of Patent: Dec. 13, 2011

(54) PROCESS FOR THE PREPARATION OF AROMATIC N-GYLCIDYL AMINES

(75) Inventors: Roger Malherbe, Muttenz (CH); Jean-Marc Pfefferle, Brent (CH)

(73) Assignee: Huntsman Advanced Materials Americas LLC, The Woodlands, TX (US)

( * ) Notice: Subject to any disclaimer, the term of this patent is extended or adjusted under 35 U.S.C. 154(b) by 1047 days.

(21) Appl. No.: 10/560,982

(22) PCT Filed: Jun. 28, 2004

(86) PCT No.: PCT/EP2004/051275
§ 371 (c)(1), (2), (4) Date: Mar. 21, 2008

(87) PCT Pub. No.: WO2005/003109
PCT Pub. Date: Jan. 13, 2005

(65) Prior Publication Data
US 2008/0221342 A1 Sep. 11, 2008

(30) Foreign Application Priority Data

Jun. 30, 2003 (CH) ..................................... 1150/03

(51) Int. Cl.
*C07D 301/27* (2006.01)
*C07D 303/08* (2006.01)
(52) U.S. Cl. ........................................ 549/552; 549/514
(58) Field of Classification Search .................... 528/90; 549/514, 552
See application file for complete search history.

(56) References Cited

U.S. PATENT DOCUMENTS 4,540,769 A * 9/1985 Dobinson et al. ............... 528/90

OTHER PUBLICATIONS

Christian Reichardt, Solvents and Solvent Effects in Organic Chemistry, Wiley-Vch Verlag Gmbh & Co. 3rd ed., 2003, p. 471-507.*

* cited by examiner

*Primary Examiner* — Taylor Victor Oh

(57) ABSTRACT

A process for the preparation of aromatic N-glycidylamines is described, wherein an amine which contains at least one aromatic aminehydrogen atom is heated with at least 0.7 equivalent of epichlorohydrin per aminehydrogen equivalent of the aromatic amine, using a divalent or polyvalent metal salt of nitric acid, as a catalyst, dissolved in propylene carbonate, and the product is then dehydrochiorinated.

6 Claims, No Drawings

PROCESS FOR THE PREPARATION OF AROMATIC N-GYLCIDYL AMINES

The present invention relates to a process for the preparation of aromatic N-glycidyl compounds, in particular those in which epoxy resins having on average more than one glycidyl group per molecule form, and the N-glycidylamines obtained thereby.

Epoxy resins are often used as adhesives, coatings, castings and insulation materials and in reinforced composites, and a large number of chemically different epoxy resins is commercially available. Such resins are usually glycidyl ethers or esters, prepared from epichlorohydrin and a bisphenol or a dicarboxylic acid. For applications which require good properties at high temperature, such as, for example, in the aviation industry, resins having glycidyl groups which are bonded to aromatic aminonitrogen atoms are often preferred. Such substances are prepared by reacting aromatic amines with about 0.8-10 equivalents of epichlorohydrin per aminohydrogen atom, followed by conventional dehydrochlorination of the products using bases. This reaction can be carried out without a catalyst or, as described in U.S. Pat. No. 4,540,769, in the presence of an acidic catalyst.

In spite of generally satisfactory properties, N-glycidylamines prepared by the known processes, and the process itself, can be further improved. A disadvantage, for example in the case of conventionally prepared N-glycidylamines, is that they are often very viscous, probably as a result of a secondary reaction during the preparation, in which a coupling reaction takes place instead of the desired glycidylation. The use of viscous resins causes difficulties, particularly in the preparation of fibre-reinforced composites or castings, with the result that the use of inert diluents, which reduce the viscosity, is often necessary. In general, the use of diluents is considered to be undesirable. Reactive diluents are those which react with the curing agent and remain in the crosslinked resin. They may have a disadvantageous effect on the properties of the cured resin. Inert diluents are removed by evaporation prior to curing and often constitute a hazard owing to their flammability or toxicity. Moreover, they may impair the properties of the cured resin unless they are removed completely from the resin. In the process used here especially on an industrial scale, there is also considerable interest in using solvents, in particular for the catalyst, which require no special safety measures or are not subject to other regulations. Finally, a high catalyst activity is desired particularly in the case of the preferably used lanthanum catalysts.

It has now been found that the process for the N-glycidylation of aromatic amines using divalent or polyvalent metal salts of nitric acid, as a catalyst, dissolved in propylene carbonate, leads to surprising advantages. One surprising advantage of the process according to the invention is the fact that the reaction takes place more rapidly than, for example, with the use of 2-methoxyethanol as a solvent for the catalyst. Furthermore surprising is the fact that, in the process according to the invention, fewer byproducts are observed compared with the use of solvents for the catalyst which are known from the literature.

The present invention therefore relates to a process for the preparation of aromatic N-glycidylamines, wherein an amine which contains at least one aromatic aminehydrogen atom and preferably at least two aromatic aminohydrogen atoms is heated with at least 0.7 equivalent and preferably at least 0.8 to 1.5 equivalents of epichlorohydrin per aminehydrogen equivalent of the aromatic amine, using a divalent or polyvalent metal salt of nitric acid, as a catalyst, dissolved in propylene carbonate, and the product is then dehydrochlorinated.

Preferably, the catalyst is completely dissolved in propylene carbonate before being added to the reaction mixture. For example, lanthanum nitrate may be used as a 5-40% strength by weight solution in propylene carbonate.

The nitrates used as catalysts in the process according to the invention are preferably salts of metals of groups IIa, IIb, IIIb, VIIb or VIII of the Periodic Table of the Elements, which may also be used in the form of hydrates. Nitrates of magnesium, of calcium, of zinc, of manganese, of nickel, of lanthanum, of vanadium (as vanadyl), of ytterbium and of uranium (as uranyl) are particularly preferred. Lanthanum nitrate is very particularly preferred, in particular in the form of the hexahydrate.

The amount of catalyst used in the reaction mixture is in general 0.1 to 10 parts by weight per 100 parts by weight of the aromatic amine, in particular 0.4 to 2 parts by weight per 100 parts by weight of the amine.

The aromatic amine which is glycidylated according to the present invention may contain only primary, only secondary, or primary and secondary amino groups which are bonded directly to an aromatic ring, and it may contain one or more aromatic rings. These aromatic rings may also be substituted by further groups, such as, for example, alkyl groups, in particular those having 1 to 4 carbon atoms, alkylene groups having 1 to 4 carbon atoms, sulphonyl groups, halogen atoms, hydroxyl groups, alkoxy groups having 1 to 4 carbon atoms and tertiary amino groups. In the present process, amines having one or two primary amino groups are preferably used. In particular anilines, aminophenylindanes and amines of the formula I or II

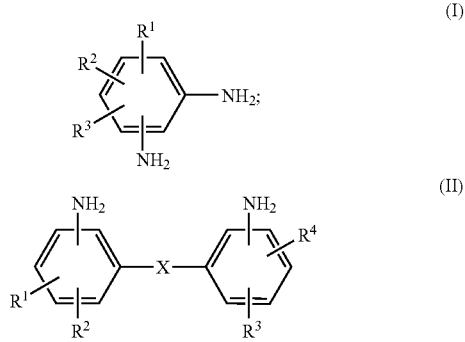

in which
$R^1$, $R^2$, $R^3$ and $R^4$ are identical or different and are alkyl groups having 1 to 4 carbon atoms or hydrogen atoms, and X is a direct bond, an alkylene group having 1 to 4 carbon atoms, an oxygen atom, a sulphur atom or a carbonyl or sulphonyl group, are particularly preferred. Examples of preferred amines are aniline, 1,1,3-trimethyl-1-(4-aminophenyl)-5-aminoindane, 1,3,3-trimethyl-1-(4-aminophenyl-6-aminoindane, o-, m- and p-phenylenediamine, 2,4-diethyl-6-methyl-1,3-phenylenediamine, bis(4-aminophenyl)methane, bis(4-aminophenyl) ketone, bis(4-aminophenyl) ether, bis(4-aminophenyl) sulphide, bis(3-amino-phenyl) and bis(4-aminophenyl) sulphone, 4,4'-diamino-3-ethyldiphenylmethane and bis(4-amino-3-ethyl-phenyl)methane, aniline and bis(4-aminophenyl)methane being very particularly preferred.

The reaction is usually carried out in an inert organic solvent, such as, for example, in toluene or xylene, at elevated temperature, in particular at 50 to 100° C. The epichlorohydrin and the catalyst can be added all at once or in portions.

After the reaction between the amine and epichlorohydrin is complete, usually after about 1 to 5 hours, the dehydrochlorination is carried out by a conventional method, in general by adding sodium hydroxide or potassium hydroxide, optionally together with a quaternary ammonium halide, such as, for example, benzyltrimethylammonium chloride, as a catalyst. After heating at 50-100° C. for 2-10 hours, the reaction mixture is washed with water and, after removal of the aqueous phase, the organic phase gives the desired N-glycidylamine. This can be used in the crude state or after purification by conventional methods.

The epoxy resins containing N-glycidyl groups and obtained by the present process can be cured in a conventional manner. Suitable curing agents for epoxy resins containing N-glycidyl groups are well known: they comprise, for example, dicyandiamide, aromatic amines, such as bis(3-aminophenyl) and bis(4-aminophenyl) sulphone and bis(4-aminophenyl)methane (generally together with a curing accelerator, such as, for example, a $BF_3$-amine complex), and anhydrides of polycarboxylic acids, such as cyclohexane-1,2-dicarboxylic anhydride, methylbicyclo[2.2.1]hept-5-ene-2,3-dicarboxylic anhydride, pyromellitic dianhydride and benzophenonetetracarboxylic dianhydride.

The following examples explain the invention in more detail. All parts and percentages are based on weight, unless stated otherwise. The viscosity determination is carried out according to ASTM-0445 (Cannon-Fenske viscometer, #650, 50° C.).

EXAMPLE 1

Bis(4-aminophenyl)methane (100 g) in 200 ml of toluene and 2.5 g of a 20% strength solution of lanthanum nitrate hexahydrate in propylene carbonate is heated to 55° C. with stirring. Epichlorohydrin (208 g) is metered in in the course of 210 minutes, after which the reaction-mixture is kept at 80° C. for a further 15 hours with stirring.

The mixture is cooled to 70° C., and 1.5 g of benzyltrimethylammonium chloride are added. A 50% strength sodium hydroxide solution (177 g) is metered in in 180 minutes and then water (326 g) is added. The aqueous phase is separated off and the organic phase is diluted with 130 g of toluene and washed with 1% strength sodium dihydrogen phosphate (75 g) and water (175 g). The toluene solution is evaporated down in vacuo at 110° C. (30 mbar) and the residue is mixed with 0.5 g of Hyflo Super Cel® (kieselgur from Fluka) and is filtered. The N-glycidylamine has an epoxide content of 8.87 eq/kg (82% of theory) and a viscosity at 50° C. of 4 270 mPas.

EXAMPLE 2

Example 1 is repeated, except that lanthanum nitrate hexahydrate is added as a finely milled powder to the amine solution in toluene. The N-glycidylamine had an epoxide content of 8.77 eq/kg (80% of theory) and a viscosity at 50° C. of 4 600 mPas.

EXAMPLE 3

Two parameters which are influenced by the kinetics and the selectivity of the reaction are measured in an experimental series. The reaction conditions are the same as in example 1, the catalyst being added in toluene, 2-methoxyethanol, ethylene carbonate, γ-butyrolactone or, according to the invention, in propylene carbonate.

TABLE 1

Comparison of the catalytic activity of various lanthanum nitrate solutions.

| Solvent | Accumulation at the end of metering | Time to crystallization [h] |
| --- | --- | --- |
| Toluene | 0.33 | 6:46 |
| 2-Methoxyethanol | 0.22 | 7:18 |
| Ethylene carbonate | 0.24 | 4:45 |
| γ-Butyrolactone | 0.23 | 6:00 |
| Propylene carbonate | 0.20 | 3:45 |

The accumulation of epichlorohydrin at the end of the metering shows whether the conversion is higher or lower. A small accumulation corresponds to a rapid reaction, i.e. also a high catalytic activity.

By the addition of 4 moles of epichlorohydrin per mole of bis(4-aminophenyl) methane, a substituted chlorohydrin forms. The time of crystallization provides information about the conversion and selectivity (purity): the earlier the better.

The invention claimed is:

1. A process for the preparation of aromatic N-glycidylamines, wherein an amine which contains at least one aromatic aminehydrogen atom is heated with at least 0.7 equivalent of epichlorohydrin per aminehydrogen equivalent of the aromatic amine, using a divalent or polyvalent metal salt of nitric acid, as a catalyst, dissolved in propylene carbonate, and the product is then dehydrochlorinated.

2. A process according to claim 1, wherein the catalyst used is lanthanum nitrate or a lanthanum nitrate hydrate.

3. A process according to claim 1, wherein the catalyst is completely dissolved in propylene carbonate before being added to the reaction mixture.

4. A process according to claim 1, wherein the amine is aniline or bis(4-aminophenyl)methane.

5. A process according to claim 1, wherein at least 0.8 to 1.5 equivalents of epichlorohydrin are used per aminehydrogen equivalent of the aromatic amine.

6. A process according to claim 1, wherein 0.1 to 10 parts by weight of catalyst are used per 100 parts by weight of the aromatic amine.

* * * * *